United States Patent

Sprague

[11] 4,061,655
[45] Dec. 6, 1977

[54] 3,6-DICARBOXIMIDAMIDECARBAZOLES

[75] Inventor: Peter W. Sprague, Titusville, N.J.

[73] Assignee: E. R. Squibb & Sons, Inc., Princeton, N.J.

[21] Appl. No.: 755,712

[22] Filed: Dec. 30, 1976

[51] Int. Cl.$^2$ ............................................ C07D 209/88
[52] U.S. Cl. .................................... 260/315; 424/274
[58] Field of Search ......................................... 260/315

[56] References Cited

U.S. PATENT DOCUMENTS 3,538,112 11/1970 Bell ...................................... 260/315

Primary Examiner—Henry R. Jiles
Assistant Examiner—R. Ramsuer

Attorney, Agent, or Firm—Lawrence S. Levinson; Merle J. Smith; Donald J. Barrack

[57] ABSTRACT

Compounds having the formula

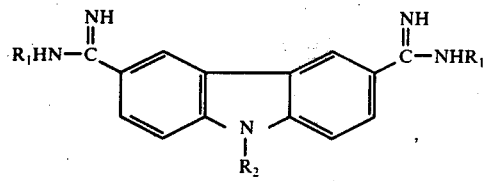

wherein $R_1$ is aryl and $R_2$ is alkyl or arylalkyl, have useful antiinflammatory activity.

10 Claims, No Drawings

3,6-DICARBOXIMIDAMIDECARBAZOLES

BRIEF DESCRIPTION OF THE INVENTION

Compounds having the formula

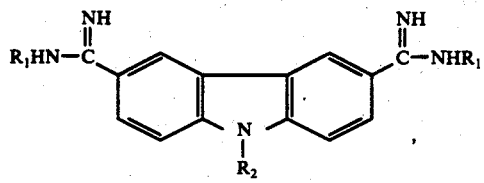

and the pharmaceutically acceptable salts thereof, have useful antiinflammatory activity. In formula I, and throughout the specification, the symbols are as defined below.

$R_1$ is phenyl or phenyl substituted with one or two methoxy, halogen or trifluoromethyl groups.

$R_2$ is alkyl or arylalkyl.

The terms "alkyl" and "alkoxy", as used throughout the specification, refer to groups having 1 to 4 carbon atoms.

The term "halogen", as used throughout the specification, refers to fluorine, chlorine, bromine and iodine.

The term "aryl", as used throughout the specification, refers to phenyl and phenyl substituted with one or two alkyl, alkoxy, halogen, or trifluoromethyl groups.

DETAILED DESCRIPTION OF THE INVENTION

The compounds of this invention are prepared by reacting a 3,6-dicyanocarbazole derivative having the formula

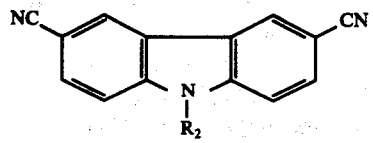

with an aniline derivative having the formula $R_1$—$NH_2$,             III in the presence of a reducing agent (sodium hydride is preferred). The reaction can be run in an organic solvent, preferably a polar organic solvent such as dimethylformamide or dimethylsulfoxide. Conditions under which the reaction is run are not critical, and it can conveniently be carried out at room temperature.

The 3,6-dicyanocarbazole derivatives of formula II can be prepared from carbazole. Using procedures known in the art, carbazole can be converted to 3,6-dihalocarbazole. Exemplary of the known methods is the reaction of carbazole and bromine in carbon disulfide under reflux conditions. The reaction of the resultant 3,6-dihalocarbazole with cuprous cyanide can be carried out, as is known in the art, in a polar organic solvent such as dimethylformamide or dimethylsulfoxide, and yields 3,6-dicyanocarbazole.

Alkylation of 3,6-dicyanocarbazole to yield a 3,6-dicyanocarbazole derivative of formula II, can be carried out using art recognized procedures. For example, 3,6-dicyanocarbazole can be reacted with an appropriate base, e.g., sodium hydride or thallous ethoxide, to obtain a salt having the structure

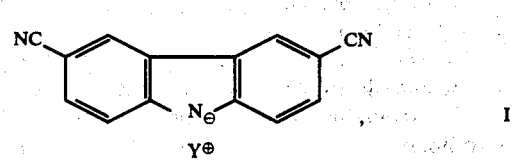

wherein Y is a cation. The salt of formula IV is subsequently reacted with a compound having the formula $R_2$—X             V wherein X is chlorine, bromine, iodine, alkylsulfonate, or arylsulfonate, to obtain a 3,6-dicyanocarbazole of formula II.

The pharmaceutically acceptable salts of the compounds of formula I can be prepared from the corresponding free base using procedures well known in the art. Acid-addition salts are specifically contemplated, e.g., the hydrohalides (especially the hydrochloride and hydrobromide), sulfate, nitrate, phosphate, tartrate, maleate, fumarate, citrate, succinate, methanesulfonate, benzenesulfonate, toluenesulfonate and the like.

The compounds of formula I, and the pharmaceutically acceptable salts thereof, are useful for the treatment of inflammation in mammalian species, such as rats, dogs, cats, monkeys, etc. Joint tenderness and stiffness (in conditions such as rheumatoid arthritis) can be relieved by the abovedescribed compounds.

The compounds of this invention can be formulated for use as antiinflammatory agents according to accepted pharmaceutical practice in oral dosage forms such as tablets, capsules, elixirs or powders, or in an injectable form in a sterile aqueous vehicle prepared according to conventional pharmaceutical practice. The compounds of this invention can be administered in amounts of 100 milligrams per kilogram of animal body weight per day to 2 grams per kilogram of animal body weight per day, preferably 100 milligrams per kilogram of animal body weight per day to 1 gram per kilogram of animal body weight per day.

The following examples are specific embodiments of this invention.

EXAMPLE 1

9-Butyl-N,N"-diphenyl-9H-carbazole-3,6-dicarboximidamide, hydrochloride (1:2)

A. 3,6-Dibromocarbazole

Carbazole (50 g) is slurried in 1200 ml of carbon disulfide and heated on a steam bath. A solution of bromine (34 ml) in 130 ml of carbon disulfide is added dropwise to the refluxing mixture over thirty minutes. After refluxing an additional five minutes, the reaction mixture is chilled in an ice bath. The resultant precipitate is collected by filtration and recrystallized from ethanol to yield 33.3 g of the title compound, melting point 210°–213° C.

B. 3,6-Dicyanocarbazole

A slurry of 3,6-dibromocarbazole (33.3 g) and cuprous cyanide (39 g) in 50 ml of dimethylformamide is heated at 160° C for seven days. The reaction mixture is poured into 1 liter of aqueous ethylenediamine (20%, v/v) and the mixture is stirred for fifteen minutes and filtered. The precipitate is slurried in 1 liter of aqueous ethylenediamine (20%, v/v) and stirred for about 16 hours. The precipitate is collected by filtration and recrystallized from dimethylformamide to yield 15 g of 3,6-dicyanocarbazole, melting point 360° C.

C. 9-Butyl-3,6-dicyanocarbazole

A slurry of sodium hydride (50% in oil, 480 mg) in 50 ml of anhydrous dimethylformamide is treated with 3,6-dicyanocarbazole (2.17 g) and heated at 110° C for two hours. The reaction mixture is then treated dropwise with butylbromide (1.37 g) and heated for about 16 hours at 110° C. The reaction mixture is poured into water and the resultant precipitate collected by filtration. The solid is dissolved in dichloromethane and filtered through 200 ml of silica gel to yield 2.22 g of the title compound, melting point 215°–217°C.

D. 9-Butyl-N,N''-diphenyl-9H-carbazole-3,6-dicarboximidamide, hydrochloride (1:2)

A slurry of sodium hydride (50% in oil, 781 mg), 9-butyl-3,6-dicyanocarbazole (2.22 g) and aniline (1.51 g) in 30 ml of anhydrous dimethylsulfoxide is stirred at room temperature for 24 hours. The reactive mixture is poured into water and extracted with dichloromethane. The dichloromethane extract is washed with water and brine, dried over sodium sulfate and concentrated. The residue is dissolved in four liters of water containing 50 ml of 10% hydrochloric acid. This solution is washed with dichloromethane, neutralized with 10% sodium hydroxide solution and extracted with dichloromethane. The dichloromethane extract is dried over sodium sulfate and concentrated. The resultant solid is recrystallized first from ethanol then from 10% hydrochloric acid to yield 1.2 g of the title compound, melting point 81°–83° C.

Anal. Calc'd. for $C_{30}H_{29}N_5.2$ $HCl.H_2O$: C, 65.45; H, 6.04; N, 12.72; Cl, 12.88. Found: C, 65.71; H, 6.26; N, 12.75; Cl, 12.91.

EXAMPLE 2

9-Butyl-N,N''-bis[3-(trifluoromethyl)phenyl]-9H-carbazole-3,6-dicarboximidamide, hydrochloride (1:2)

A slurry of 9-butyl-3,6-dicyanocarbazole (4 g, see Example 1C) and sodium hydride (50% in oil, 1.41 g) in 20 ml of anhydrous dimethylsulfoxide is treated dropwise with m-trifluoromethylaniline (4.72 g). The reaction mixture is stirred at room temperature for four days and then poured into 500 ml of water and stirred vigorously for two hours. The resultant precipitate is collected by filtration and purified by column chromatography using one liter of silica gel. Elution with dichloromethane and 1% ethyl acetate/dichloromethane yields 1.8 g of 9-butyl-6-cyano-N-[3-(trifluoromethyl)phenyl]-9H-carbazole-3-carboximidamide. Elution with 20% ethyl acetate/dichloromethane and ethyl acetate/dichloromethane/methanol (2:7:1) yields 1.6 g of the desired diamidine, which is recrystallized from two liters of water containing 15 ml of 10% hydrochloric acid to yield 1.5 g of the title compound, melting point 205°–210° C.

Anal. Calc'd. for $C_{32}H_{27}N_5F_6 \cdot 2$ HCl. 2.4 $H_2O$: C, 54.00; H, 4.79; N, 9.84; Cl, 9.96. Found: C, 54.01; H, 4.61; N, 9.94; Cl, 10.04.

EXAMPLE 3

N,N''-Diphenyl-9-(phenylmethyl)-9H-carbazole-3,6-dicarboximidamide, hydrochloride (1:2)

A. 9-Benzyl-3,6-dicyanocarbazole

A slurry of sodium hydride (50% in oil, 960 mg) in 100 ml of dimethylformamide is treated with 3,6-dicyanocarbazole (4.34 g, see Example 1) and heated at 110° C for two hours. The reaction mixture is then treated dropwise with benzylbromide (3.42 g) and heated at 110° C for an additional 18 hours. The reaction mixture is poured into water and extracted several times with dichloromethane. The combined dichloromethane extracts are dried over sodium sulfate and filtered through 200 ml of silica gel to yield 4.9 g of the title compound, melting point 265°–267° C.

B. N,N''-Diphenyl-9-(phenylmethyl)-9H-carbazole-3,6-dicarboximidamide, hydrochloride A slurry of sodium hydride (50% in oil, 760 mg), 9-benzyl-3,6-dicyanocarbazole (2.43 g) and aniline (1.47 g) in 30 ml of anhydrous dimethylsulfoxide is stirred at room temperature for 24 hours and then poured into water and extracted with dichloromethane. The dichloromethane extract is washed with water and brine, dried over sodium sulfate and concentrated. The residue is dissolved in eight liters of water containing 100 ml of 10% hydrochloric acid. The acid solution is washed with dichloromethane, neutralized with 10% sodium hydroxide, and again extracted with dichloromethane. This extract is dried over sodium sulfate, concentrated, and the resultant solid recrystallized once from ethanol and then from 10% hydrochloric acid to yield 750 mg of the title compound, melting point 230°–240° C.

Anal. Calc'd. for $C_{33}H_{27}N_5.2$ HCl.2 $H_2O$: C, 65.54; H, 5.38; N, 11.81; Cl, 11.76. Found: C, 65.77; H, 5.52; N, 11.62; Cl, 11.98.

EXAMPLE 4

9-(Phenylmethyl)-N,N''-bis[3-(trifluoromethyl)phenyl]-9H-carbazole-3,5-dicarboximidamide, hydrochloride (1:2)

A slurry of 9-benzyl-3,6-dicyanocarbazole (3.8 g, see Example 3C) and sodium hydride (50% in oil, 1.21 g) in 20 ml of dimethylsulfoxide is treated dropwise with m-trifluoromethylaniline (4.04 g). The reaction mixture is stirred at room temperature for four days and then poured into 500 ml of water and stirred vigorously for two hours. The resultant precipitate is collected by filtration and purified by column chromatography using one liter of silica gel. Elution with dichloromethane and 1% ethyl acetate/dichloromethane yields 1.5 g of 6-cyano-9-(phenylmethyl)-N-[3-(trifluoromethyl)phenyl]-3-carbazolecarboximidamide. Elution with 20% ethyl acetate/dichloromethane/methanol (2:7:1) yields 2g of the desired diamidine, which is recrystallized from two liters of water containing 10 ml of concentrated hydrochloric acid to yield 1.6 g of the title compound, melting point 210°–220° C.

Anal. Calc'd. for $C_{35}H_{25}N_5F_6.2$ HCl.3 $H_2O$: C, 55.56; H, 4.40; N, 9.26; Cl, 9.37. Found: C, 55.27; H, 4.30; N, 9.31; Cl, 9.21.

EXAMPLES 5–10

Following the procedure of Example 1, but substituting the compound listed in column I for butylbromide and the compound listed in column II for aniline, yields the compound listed in column III.

| Column I | Column II | Column III |
|---|---|---|
| methyl iodide | p-fluoroaniline | 9-methyl-N,N''-bis[4-fluorophenyl]-9H-carbazole-3,6-dicarboximidamide, dihydrochloride |
| 4-bromo-1-phenylbutane | 3,5-dimethoxyaniline | 9-(4-phenylbutyl)-N,N''-bis[3,5-dimethoxyphenyl]-9H-carbazole-3,6-dicarboximidamide, dihydrochloride |
| 3-bromo-1-(2-chlorophenyl)butane | m-trifluoromethylaniline | 9-[3-(2-chlorophenyl)-1-methylpropyl]-N,N''-bis[3-trifluoromethylphenyl]-9H-carbazole-3,6-dicarboximidamide, dihydrochloride |
| 2-bromo-1-(3,5-dimethylphenyl)ethane | 3,4-dichloroaniline | 9-[2-(3,5-dimethylphenyl)ethyl]-N,N''-bis[3,5-dichlorophenyl]-9H-carbazole-3,6-dicarboximidamide, dihydrochloride |
| p-methoxybenzyl bromide | aniline | 9-[(4-methoxyphenyl)methyl]-N,N''-diphenyl-9H-carbazole-3,6-dicarboximidamide |
| 4-bromo-1-(3-trifluoromethylphenyl)butane | aniline | 9-[4-(3-trifluoromethylphenyl)butyl]-N,N''-diphenyl-9H-carbazole-3,6-dicarboximidamide |

What is claimed is:

1. A compound having the formula

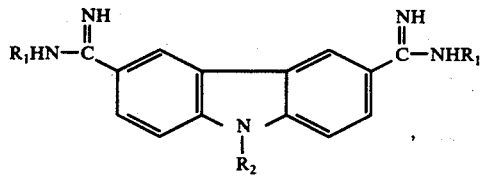

or a pharmaceutically acceptable salt thereof, wherein $R_1$ is phenyl or phenyl substituted with one or two methoxy, halogen or trifluoromethyl groups and $R_2$ is alkyl or arylalkyl; wherein alkyl is alkyl of 1 to 4 carbon atoms and aryl is phenyl or phenyl substituted with one or two alkyl, alkoxy of 1 to 4 carbon atoms, halogen or trifluoromethyl groups.

2. A compound in accordance with claim 1 wherein $R_1$ is phenyl.

3. A compound in accordance with claim 1 wherein $R_1$ is 3-trifluoromethylphenyl.

4. A compound in accordance with claim 1 wherein $R_2$ is alkyl.

5. A compound in accordance with claim 4 wherein $R_2$ is butyl.

6. A compound in accordance with claim 1 wherein $R_2$ is phenylmethyl.

7. The compound in accordance with claim 1 having the name 9-butyl-N,N''-diphenyl-9H-carbazole-3,6-dicarboximidamide, hydrochloride (1:2).

8. The compound in accordance with claim 1 having the name 9-butyl-N,N''-bis[3-(trifluoromethyl)phenyl]-9H-carbazole-3,6-dicarboximidamide, hydrochloride (1:2).

9. The compound in accordance with claim 1 having the name N,N''-diphenyl-9-(phenylmethyl)-9H-carbazole-3,6-dicarboximidamide, hydrochloride (1:2).

10. The compound in accordance with claim 1 having the name 9-(phenylmethyl)-N,N''-bis[3-(trifluoromethyl)phenyl]-9H-carbazole-3,5-dicarboximidamide, hydrochloride (1:2).

* * * * *